United States Patent
Colvin, Jr. et al.

(10) Patent No.: US 7,822,450 B2
(45) Date of Patent: Oct. 26, 2010

(54) OPTICAL-BASED SENSING DEVICES

(75) Inventors: Arthur E. Colvin, Jr., Mt. Airy, MD (US); Casey J. O'Connor, Gaithersburg, MD (US); Andrew D. DeHennis, Germantown, MD (US)

(73) Assignee: Sensors for Medicine and Science, Inc., Germantown, MD (US)

( * ) Notice: Subject to any disclaimer, the term of this patent is extended or adjusted under 35 U.S.C. 154(b) by 0 days.

(21) Appl. No.: 11/953,166

(22) Filed: Dec. 10, 2007

(65) Prior Publication Data

US 2008/0139904 A1    Jun. 12, 2008

Related U.S. Application Data

(63) Continuation of application No. 11/106,481, filed on Apr. 15, 2005, now Pat. No. 7,308,292.

(51) Int. Cl.
*A61B 5/145* (2006.01)
(52) U.S. Cl. .................. 600/310; 600/317
(58) Field of Classification Search .......... 600/309, 600/310, 316, 317, 322, 341
See application file for complete search history.

(56) References Cited

U.S. PATENT DOCUMENTS

| | | | |
|---|---|---|---|
| 3,229,684 A | 1/1966 | Nagumo et al. | |
| 3,399,667 A | 9/1968 | Nishimoto et al. | |
| 3,576,554 A | 4/1971 | Temps, Jr. et al. | |
| 3,612,866 A | 10/1971 | Stevens | |
| 3,649,833 A | 3/1972 | Leaf | |
| 3,800,300 A | 3/1974 | Van Oosterhout | |
| 3,839,708 A | 10/1974 | Bredesen et al. | |
| 3,853,117 A | 12/1974 | Murr | |
| 3,872,455 A | 3/1975 | Fuller et al. | |
| 3,893,111 A | 7/1975 | Cotter | |
| 3,949,388 A | 4/1976 | Fuller | |
| 3,972,320 A | 8/1976 | Kalman | |
| 4,041,954 A | 8/1977 | Ohara | |
| 4,160,971 A | 7/1979 | Jones et al. | |

(Continued)

FOREIGN PATENT DOCUMENTS

DE    4341903 A1    6/1995

(Continued)

OTHER PUBLICATIONS

Jie Lin et al. "Sol-gel glass as a matrix for chemical and biochemical sensing" *Trends in Analytical Chemistry*, 16(4):200-211 (1997).

(Continued)

*Primary Examiner*—Eric F Winakur
*Assistant Examiner*—Etsub D Berhanu
(74) *Attorney, Agent, or Firm*—Rothwell, Figg, Ernst & Manbeck, PC (57) ABSTRACT

The present invention provides an electro-optical sensing device for detecting the presence or concentration of an analyte. More particularly, the invention relates to (but is not in all cases necessarily limited to) optical-based sensing devices which are characterized by being totally self-contained, with a smooth and rounded oblong, oval, or elliptical shape (e.g., a bean- or pharmaceutical capsule-shape) and a size which permits the device to be implanted in humans for in-situ detection of various analytes.

18 Claims, 6 Drawing Sheets

U.S. PATENT DOCUMENTS

| | | |
|---|---|---|
| 4,186,749 A | 2/1980 | Fryer |
| 4,262,632 A | 4/1981 | Hanton et al. |
| 4,313,262 A | 2/1982 | Barnes et al. |
| 4,361,153 A | 11/1982 | Slocum et al. |
| 4,401,122 A | 8/1983 | Clark, Jr. |
| 4,531,526 A | 7/1985 | Genest |
| 4,677,008 A | 6/1987 | Webb |
| 4,680,268 A | 7/1987 | Clark, Jr. |
| 4,703,756 A | 11/1987 | Gough et al. |
| 4,704,029 A | 11/1987 | Van Heuvelen |
| 4,730,188 A | 3/1988 | Milheiser |
| 4,737,464 A | 4/1988 | McConnell et al. |
| 4,746,830 A | 5/1988 | Holland |
| 4,752,115 A | 6/1988 | Murray, Jr. et al. |
| 4,755,667 A | 7/1988 | Marsoner |
| 4,854,328 A | 8/1989 | Pollack |
| 4,863,470 A | 9/1989 | Carter |
| 4,875,483 A | 10/1989 | Vollmann et al. |
| 4,935,632 A | 6/1990 | Hart |
| 4,992,794 A | 2/1991 | Brouwers |
| 5,001,054 A | 3/1991 | Wagner |
| 5,010,893 A | 4/1991 | Sholder |
| 5,012,286 A | 4/1991 | Kawano et al. |
| 5,028,918 A | 7/1991 | Giles et al. |
| 5,036,869 A | 8/1991 | Inahara |
| 5,039,490 A | 8/1991 | Marsoner et al. |
| 5,041,826 A | 8/1991 | Milheiser |
| 5,084,699 A | 1/1992 | DeMichele |
| 5,095,309 A | 3/1992 | Troyk et al. |
| 5,117,825 A | 6/1992 | Grevious |
| 5,143,066 A | 9/1992 | Komives et al. |
| 5,157,262 A | 10/1992 | Marsoner et al. |
| 5,211,129 A | 5/1993 | Taylor et al. |
| 5,218,343 A | 6/1993 | Stobbe et al. |
| 5,235,326 A | 8/1993 | Beigel et al. |
| 5,244,810 A | 9/1993 | Gottlieb |
| 5,281,825 A | 1/1994 | Berndt et al. |
| 5,300,120 A | 4/1994 | Knapp et al. |
| 5,302,393 A | 4/1994 | Matsumoto et al. |
| 5,314,457 A | 5/1994 | Jeutter et al. |
| 5,341,805 A | 8/1994 | Stavridi et al. |
| 5,342,789 A | 8/1994 | Chick et al. |
| 5,372,133 A | 12/1994 | Hogen Esch |
| 5,517,313 A | 5/1996 | Colvin, Jr. |
| 5,584,870 A | 12/1996 | Single et al. |
| 5,628,310 A | 5/1997 | Rao et al. |
| 5,630,836 A | 5/1997 | Prem et al. |
| 5,633,724 A | 5/1997 | King et al. |
| 5,674,288 A | 10/1997 | Knapp et al. |
| 5,682,149 A | 10/1997 | Hofman |
| 5,704,352 A | 1/1998 | Tremblay et al. |
| 5,708,957 A | 1/1998 | Chuang et al. |
| 5,725,578 A | 3/1998 | Knapp et al. |
| 5,730,125 A | 3/1998 | Prutchi et al. |
| 5,735,887 A | 4/1998 | Barreras, Sr. et al. |
| 5,833,603 A | 11/1998 | Kovacs et al. |
| 5,855,609 A | 1/1999 | Knapp |
| 5,922,285 A | 7/1999 | Melendez et al. |
| 5,939,609 A | 8/1999 | Knapp et al. |
| 5,963,132 A | 10/1999 | Yoakum |
| 5,966,404 A | 10/1999 | Yokota et al. |
| 5,977,431 A | 11/1999 | Knapp et al. |
| 5,995,860 A | 11/1999 | Sun et al. |
| 6,002,954 A | 12/1999 | Van Antwerp et al. |
| 6,009,878 A | 1/2000 | Weijand et al. |
| 6,011,984 A | 1/2000 | Van Antwerp et al. |
| 6,040,194 A | 3/2000 | Chick et al. |
| 6,073,050 A | 6/2000 | Griffith |
| 6,092,530 A | 7/2000 | Weissman et al. |
| 6,099,482 A | 8/2000 | Brune et al. |
| 6,141,591 A | 10/2000 | Lenarz et al. |
| 6,179,767 B1 | 1/2001 | Ziegler et al. |
| 6,198,950 B1 | 3/2001 | Kraus |
| 6,201,607 B1 | 3/2001 | Roth et al. |
| 6,212,431 B1 | 4/2001 | Hahn et al. |
| 6,259,937 B1 | 7/2001 | Schulman et al. |
| 6,268,161 B1 | 7/2001 | Han et al. |
| 6,289,229 B1 | 9/2001 | Crowley |
| 6,304,766 B1 | 10/2001 | Colvin, Jr. |
| 6,321,067 B1 | 11/2001 | Suga et al. |
| 6,330,464 B1 | 12/2001 | Colvin et al. |
| 6,330,885 B1 | 12/2001 | Weissman et al. |
| 6,368,275 B1 | 4/2002 | Sliwa et al. |
| 6,387,048 B1 | 5/2002 | Schulman et al. |
| 6,400,974 B1 | 6/2002 | Lesho |
| 6,411,108 B1 | 6/2002 | Douglas et al. |
| 6,415,186 B1 | 7/2002 | Chim et al. |
| 6,419,624 B1 | 7/2002 | Burton et al. |
| 6,424,847 B1 | 7/2002 | Mastrototaro et al. |
| 6,430,444 B1 | 8/2002 | Borza |
| 6,443,891 B1 | 9/2002 | Grevious |
| 6,447,448 B1 | 9/2002 | Ishikawa et al. |
| 6,454,710 B1 | 9/2002 | Ballerstadt et al. |
| 6,475,750 B1 | 11/2002 | Han et al. |
| 6,505,059 B1 | 1/2003 | Kollias et al. |
| 6,542,777 B1 | 4/2003 | Griffith et al. |
| 6,545,483 B1 | 4/2003 | Douglas |
| 6,564,807 B1 | 5/2003 | Schulman et al. |
| 6,585,763 B1 | 7/2003 | Keilman et al. |
| 6,614,406 B2 | 9/2003 | Amundson et al. |
| 6,649,416 B1 | 11/2003 | Kauer et al. |
| 6,666,821 B2 | 12/2003 | Keimel |
| 6,671,527 B2 | 12/2003 | Petersson et al. |
| 6,682,490 B2 | 1/2004 | Roy et al. |
| 6,694,158 B2 | 2/2004 | Polak |
| 6,711,423 B2 | 3/2004 | Colvin, Jr. |
| 6,731,961 B2 | 5/2004 | Braig et al. |
| 6,731,976 B2 | 5/2004 | Penn et al. |
| 6,772,011 B2 | 8/2004 | Dolgin |
| 6,802,811 B1 | 10/2004 | Slepian |
| 6,806,552 B2 | 10/2004 | Woo et al. |
| 6,809,507 B2 | 10/2004 | Morgan et al. |
| 6,809,653 B1 | 10/2004 | Mann et al. |
| 6,809,701 B2 | 10/2004 | Amundson et al. |
| 6,882,538 B1 | 4/2005 | Frisch |
| 6,940,590 B2 | 9/2005 | Colvin, Jr. et al. |
| 2002/0016535 A1 | 2/2002 | Martin et al. |
| 2002/0019707 A1 | 2/2002 | Cohen et al. |
| 2002/0026108 A1* | 2/2002 | Colvin, Jr. .................. 600/316 |
| 2002/0032435 A1 | 3/2002 | Levin |
| 2002/0118134 A1 | 8/2002 | Chen |
| 2002/0123779 A1 | 9/2002 | Zarinetchi et al. |
| 2002/0161288 A1 | 10/2002 | Shin et al. |
| 2002/0164813 A1 | 11/2002 | Colvin, Jr. et al. |
| 2003/0025645 A1 | 2/2003 | Amundson et al. |
| 2003/0050542 A1 | 3/2003 | Reihl et al. |
| 2003/0098783 A1 | 5/2003 | Pagnol |
| 2003/0113934 A1 | 6/2003 | Kwon |
| 2003/0125612 A1 | 7/2003 | Fox et al. |
| 2003/0140931 A1 | 7/2003 | Zeijlemaker et al. |
| 2003/0169169 A1 | 9/2003 | Wuidart et al. |
| 2003/0172940 A1 | 9/2003 | Rogers et al. |
| 2003/0195400 A1 | 10/2003 | Glukhovsky |
| 2003/0213495 A1 | 11/2003 | Fujita et al. |
| 2004/0027306 A1 | 2/2004 | Amundson et al. |
| 2004/0048394 A1 | 3/2004 | Kirchhevel |
| 2004/0147801 A1 | 7/2004 | Kugler et al. |
| 2004/0176669 A1 | 9/2004 | Colvin, Jr. |
| 2004/0181155 A1 | 9/2004 | Glukhovsky |
| 2004/0199059 A1 | 10/2004 | Brauker et al. |

FOREIGN PATENT DOCUMENTS

| | | |
|---|---|---|
| DE | 19615380 A1 | 3/1997 |

| | | | |
|---|---|---|---|
| DE | 19826294 C1 | 2/2000 | |
| EP | 0309214 A2 | 3/1989 | |
| EP | 0309214 A3 | 3/1989 | |
| EP | 097566 A1 | 5/1994 | |
| EP | 0619101 A1 | 10/1994 | |
| EP | 0646313 A1 | 4/1995 | |
| EP | 0693271 A1 | 1/1996 | |
| EP | 0834734 A2 | 4/1998 | |
| EP | 0834734 A3 | 4/1998 | |
| FR | 2680672 A1 | 3/1993 | |
| GB | 2258589 A | 2/1993 | |
| TW | 200303984 A | 9/2003 | |
| WO | WO 87/04900 A1 | 8/1987 | |
| WO | WO 92/07505 A1 | 5/1992 | |
| WO | WO 96/16593 A1 | 6/1996 | |
| WO | WO 96/25978 A1 | 8/1996 | |
| WO | WO 97/33513 A1 | 9/1997 | |
| WO | WO 98/52023 A1 | 11/1998 | |
| WO | WO 99/66309 A1 | 12/1999 | |
| WO | WO 02/078532 A1 | 10/2002 | |
| WO | 02090951 A1 | 11/2002 | |

OTHER PUBLICATIONS

Alan Baron et al. "Submillisecond response times of oxygen-quenched luminescent coatings" *Rev. Sci. Instrum.* 64(12):3394-3402 (1993).

Brauker et al., "Neovascularization of synthetic membranes directed by membrane microarchitecture", *Journal of Biomedical Materials Research*, vol. 29, 1517-1524 (1995).

Chuang and Arnold,"Radioluminescent Light Source for Optical Oxygen Sensors", *Analytical Chemistry*, vol. 69, No. 10, 1899-1903, 1997.

Geller, et al., "Immunoisolation of Tumor Cells: Generation of Antitumor Immunity Through Indirect Presentation of Antigen", *Journal of Immunotherapy*, 20(2):131-137 (1997).

Shamlou et al, "Amphiphilic networks. X. Diffusion of glucose and insulin (and nondiffusion of albumin) through amphiphilic membranes", *Journal of Biomedical Materials Research*, vol. 35, 157-163 (1997).

Kennedy, "Tailoring polymers for biological uses" *Chemtech*, pp. 24-32, Feb. 1994.

Tuan, "Recombinant Protein Protocols, Detection and Isolation", *Methods in Molecular Biology*, vol. 63, pp. 373-387.

Ward, "Development of a Hybrid Artificial Pancreas with a Dense Polyurethane Membrane", *ASAIO Journal*, vol. 39, No. 3, pp. M261-M267, 1993.

Wilkins, "Biomaterials for Implanted Closed Loop Insulin Delivery System: A Review", *Biosensors and Bioelectronics 5*, pp. 167-203, 1990.

Advertisement pamphlet entitled "RFID: Everything you need to know" by Motorola Indala Corporation, 1996, 1997 (5 pages).

Pamphlet entitled "Divvying up the biostent market", *BioCentury, The Bernstein Report on BioBusiness*, pp. A6, Aug. 10, 1998.

Advertising pamphlet entitled "Biocompatibility, controlled porosity, inertness, strength and comformability.", *Gore-Tex Medical Products*, 1990 (4 pages).

Product pamphlet for "Preclude Pericardial Membrane", *W.L. Gore & Associates, Inc.*, 1996 (2 pages).

Product pamphlet for "The Duraflo® Biocompatible Treatment", *Baxter Healthcare Corporation*, 1995 (4 pages).

O'Toole, et al. "Laminin-5 inhibits human keratinocyte migration", *Exp Cell Res*, 233:2 330-9, 1997 (abstract only).

Wouters et al., "A Low Power Multi-Sensor Interface for Injectable Microprocessor-Based Animal Monitoring System" *Sensors and Acutuators A*, 41-42 (1994) 198-206.

"DIOG Database Guide (Standard Search Service)" SRS Information Technologies, 1987 (7 pages).

* cited by examiner

OPTICAL-BASED SENSING DEVICES

CROSS-REFERENCE TO RELATED APPLICATIONS

This application is a continuation of application Ser. No. 11/106,481, filed on Apr. 15, 2005, the contents of which are hereby incorporated by reference in their entirety.

BACKGROUND OF THE INVENTION

1. Field of the Invention

The invention relates to electro-optical sensing devices for detecting the presence or concentration of an analyte in a liquid or gaseous medium. More particularly, the invention relates to (but is not in all cases necessarily limited to) optical-based sensing devices which are characterized by being totally self-contained, with a smooth and rounded oblong, oval, or elliptical shape (e.g., a bean- or pharmaceutical capsule-shape) and a size which permit the device to be implanted in humans for in-situ detection of various analytes.

2. Discussion of the Background

U.S. Pat. No. 5,517,313, the disclosure of which is incorporated herein by reference, describes a fluorescence-based sensing device comprising indicator molecules and a photosensitive element, e.g., a photodetector. Broadly speaking, in the context of the field of the present invention, indicator molecules are molecules one or more optical characteristics of which is or are affected by the local presence of an analyte. In the device according to U.S. Pat. No. 5,517,313, a light source, e.g., a light-emitting diode ("LED"), is located at least partially within a layer of material containing fluorescent indicator molecules or, alternatively, at least partially within a wave guide layer such that radiation (light) emitted by the source strikes and causes the indicator molecules to fluoresce. A high-pass filter allows fluorescent light emitted by the indicator molecules to reach the photosensitive element (photodetector) while filtering out scattered light from the light source.

The fluorescence of the indicator molecules employed in the device described in U.S. Pat. No. 5,517,313 is modulated, i.e., attenuated or enhanced, by the local presence of an analyte. For example, the orange-red fluorescence of the complex tris(4,7-diphenyl-1,10-phenanthroline)ruthenium(II) perchlorate is quenched by the local presence of oxygen. Therefore, this complex can be used advantageously as the indicator molecule in an oxygen sensor. Indicator molecules whose fluorescence properties are affected by various other analytes are known as well.

Furthermore, indicator molecules which absorb light, with the level of absorption being affected by the presence or concentration of an analyte, are also known. See, for example, U.S. Pat. No. 5,512,246, the disclosure of which is incorporated by reference, which discloses compositions whose spectral responses are attenuated by the local presence of polyhydroxyl compounds such as sugars. It is believed, however, that such light-absorbing indicator molecules have not been used before in a sensor construct like that taught in U.S. Pat. No. 5,517,313 or in a sensor construct as taught herein.

In the sensor described in U.S. Pat. No. 5,517,313, the material which contains the indicator molecules is permeable to the analyte. Thus, the analyte can diffuse into the material from the surrounding test medium, thereby affecting the fluorescence of the indicator molecules. The light source, indicator molecule-containing matrix material, high-pass filter, and photodetector are configured such that fluorescent light emitted by the indicator molecules impacts the photodetector such that an electrical signal is generated that is indicative of the concentration of the analyte in the surrounding medium.

The sensing device described in U.S. Pat. No. 5,517,313 represents a marked improvement over devices which constitute prior art with respect to U.S. Pat. No. 5,517,313. There has, however, remained a need for sensors that permit the detection of various analytes in an extremely important environment—the human body. Moreover, further refinements have been made in the field, which refinements have resulted in smaller and more efficient devices.

U.S. Pat. Nos. 6,400,974 and 6,711,423, the disclosures of which are incorporated herein by reference, each describe a fluorescence-based sensing device comprising indicator molecules and a photosensitive element that is designed for use in the human body.

SUMMARY OF THE INVENTION

In one aspect, the present invention provides an electro-optical sensing device. In one particular embodiment, the sensing device includes: a housing having an outer surface; a plurality of indicator molecules located on at least a portion of the outer surface of the housing; a circuit board housed within the housing; a support member having a side that lies on a plane that is substantially perpendicular to a plane on which a top side of the circuit board lies; a radiation source attached to the side of the support member and positioned a distance above the top side of the circuit board; and a photodetector connected to the circuit board for detecting a response of the indicator molecules.

Advantageously, to facilitate attachment of the support member to the circuit board, the circuit board may have a groove in the top side thereof and the support member may have an end inserted into the groove.

The sensing device may further include a reflector that is spaced apart from the radiation source and that has a reflective side that faces the radiation source. The photodetector may be positioned in a location beneath a region between the radiation source and the reflective side of the reflector.

In another embodiment, the sensing device includes: a housing having an outer surface; a plurality of indicator molecules located on at least a portion of the outer surface of the housing; a circuit board housed within the housing; a photodetector having a top side and a bottom side, wherein the photodetector is electrically connected to a circuit on the circuit board and at least a top side of the photodetector is photosensitive; a filter having a top side and a bottom side, the bottom side being positioned over the top side of the photodetector; and a radiation source positioned over the top side of the filter.

In some embodiments, the sensing device may further include a base having a top side and a bottom side, with the bottom side being attached to an end of the circuit board, and with the bottom side of the photodetector being mounted on the top side of the base. Preferably, the top side of the base lies in a plane that is substantially perpendicular to a plane on which a top side of the circuit board lies and the top side of the photodetector is generally parallel with the top side of the base. To facilitate attachment of the base to the circuit board, the bottom side of the base may have a groove therein, and an end of the circuit board may be inserted into the groove.

In other configurations, the top side of the photodetector lies in a plane that is substantially parallel with a plane on which a top side of the circuit board lies. Additionally, an opaque base may be disposed between the radiation source and the filter. The base may be made from molybdenum.

The above and other features and advantages of the present invention, as well as the structure and operation of preferred embodiments of the present invention, are described in detail below with reference to the accompanying drawings.

BRIEF DESCRIPTION OF THE DRAWINGS

The accompanying drawings, which are incorporated herein and form part of the specification, help illustrate various embodiments of the present invention and, together with the description, further serve to explain the principles of the invention and to enable a person skilled in the pertinent art to make and use the invention. In the drawings, like reference numbers indicate identical or functionally similar elements. Additionally, the left-most digit(s) of a reference number identifies the drawing in which the reference number first appears.

DETAILED DESCRIPTION OF PREFERRED EMBODIMENTS

Figure 1:
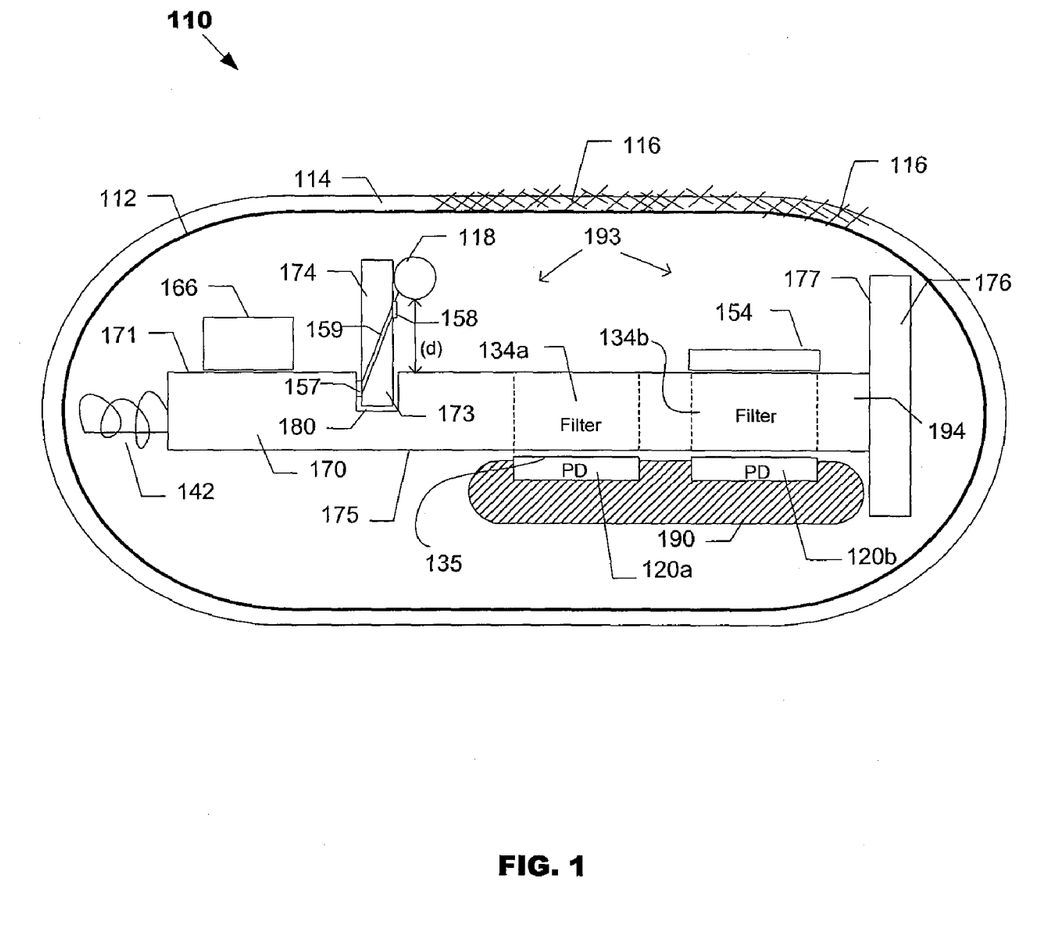
FIG. 1 is a schematic, section view of a fluorescence-based sensor according to an embodiment of the invention.

FIG. 1 is a schematic, section view of an optical-based sensor ("sensor") 110, according to an embodiment of the invention, that operates based on the fluorescence of fluorescent indicator molecules 116. As shown, sensor 110 includes a sensor housing 112. Sensor housing 112 may be formed from a suitable, optically transmissive polymer material. Preferred polymer materials include, but are not limited to, acrylic polymers such as polymethylmethacrylate (PMMA).

Sensor 110 may further include a matrix layer 114 coated on at least part of the exterior surface of the sensor housing 112, with fluorescent indicator molecules 116 distributed throughout the layer 114 (layer 114 can cover all or part of the surface of housing 112).

Sensor 110 further includes a radiation source 118, e.g. a light emitting diode (LED) or other radiation source, that emits radiation, including radiation over a range of wavelengths which interact with the indicator molecules 116. For example, in the case of a fluorescence-based sensor, radiation sensor 118 emits radiation at a wavelength which causes the indicator molecules 116 to fluoresce. Sensor 110 also includes a photodetector 120 (e.g. a photodiode, phototransistor, photoresistor or other photosensitive element) which, in the case of a fluorescence-based sensor, is sensitive to fluorescent light emitted by the indicator molecules 116 such that a signal is generated by the photodetector 120 in response thereto that is indicative of the level of fluorescence of the indicator molecules. Two photodetectors 120a and 120b are shown in FIG. 1 to illustrate that sensor 110 may have more than one photodetector. Source 118 may be implemented using, for example, LED model number EU-U32SB from Nichia Corporation (www.nichia.com). Other LEDs may be used depending on the specific indicator molecules applied to sensor 110 and the specific analytes of interested to be detected.

The indicator molecules 116 may be coated on the surface of the sensor body or they may be contained within matrix layer 114 (as shown in FIG. 1), which comprises a biocompatible polymer matrix that is prepared according to methods known in the art and coated on the surface of the sensor housing 112. Suitable biocompatible matrix materials, which preferably are permeable to the analyte, include some methacrylates (e.g., HEMA) and hydrogels which, advantageously, can be made selectively permeable—particularly to the analyte—i.e., they perform a molecular weight cut-off function.

Sensor 110 may be wholly self-contained. In other words, the sensor is preferably constructed in such a way that no electrical leads extend into or out of the sensor housing 112 to supply power to the sensor (e.g., for driving the source 118) or to transmit signals from the sensor. Rather, sensor 110 may be powered by an external power source (not shown), as is well known in the art. For example, the external power source may generate a magnetic field to induce a current in inductive element 142 (e.g., a copper coil or other inductive element). Additionally, circuitry 166 may use inductive element 142 to communicate information to an external data reader. Circuitry 166 may include discrete circuit elements, an integrated circuit (e.g., an application specific integrated circuit (ASIC), and/or other electronic components). The external power source and data reader may be the same device.

In an alternative embodiment, the sensor 110 may be powered by an internal, self-contained power source, such as, for example, microbatteries, micro generators and/or other power sources.

As shown in FIG. 1, many of the electro-optical components of sensor 110 are secured to a circuit board 170. Circuit board 170 provides communication paths between the various components of sensor 110.

As further illustrated in FIG. 1, optical filters 134a and 134b, such as high pass or band pass filters, may cover a photosensitive side of photodetectors 120a and 120b, respectively. Filter 134a may prevent or substantially reduce the amount of radiation generated by the source 118 from impinging on a photosensitive side 135 of the photodetector 120a. At the same time, filter 134a allows fluorescent light emitted by fluorescent indicator molecules 116 to pass through to strike photosensitive side 135 of the photodetector 120a. This significantly reduces "noise" in the photodetector signal that is attributable to incident radiation from the source 118.

According to one aspect of the invention, an application for which the sensor 110 was developed—although by no means the only application for which it is suitable—is measuring various biological analytes in the human body. For example, sensor 110 may be used to measure glucose, oxygen, toxins, pharmaceuticals or other drugs, hormones, and other metabolic analytes in the human body. The specific composition of the matrix layer 114 and the indicator molecules 116 may vary depending on the particular analyte the sensor is to be used to detect and/or where the sensor is to be used to detect the analyte (i.e., in the blood or in subcutaneous tissues). Preferably, however, matrix layer 114, if present, should facilitate exposure of the indicator molecules to the analyte. Also, it is preferred that the optical characteristics of the indicator molecules (e.g., the level of fluorescence of fluorescent indicator molecules) be a function of the concentration of the specific analyte to which the indicator molecules are exposed.

To facilitate use in-situ in the human body, the housing 112 is preferably formed in a smooth, oblong or rounded shape. Advantageously, it has the approximate size and shape of a bean or a pharmaceutical gelatin capsule, i.e., it is on the order of approximately 500 microns to approximately 0.85 inches in length L and on the order of approximately 300 microns to approximately 0.3 inches in diameter D, with generally smooth, rounded surfaces throughout. This configuration permits the sensor 110 to be implanted into the human body, i.e., dermally or into underlying tissues (including into organs or blood vessels) without the sensor interfering with essential bodily functions or causing excessive pain or discomfort.

In some embodiments, a preferred length of the housing is approx. 0.5 inches to 0.85 inches and a preferred diameter is approx. 0.1 inches to 0.11 inches.

In the embodiment shown in FIG. 1, source 118 is elevated with respect to a top side 171 of circuit board 170. More specifically, in the embodiment shown, source 118 is fixed to a support member 174, which functions to elevate source 118 above side 171 and to electrically connect source 118 to circuitry on board 170 so that power can be delivered to source 118. The distance (d) between source 118 and side 171 generally ranges between 0 and 0.030 inches. Preferably, the distance (d) ranges between 0.010 and 0.020 inches. Support member 174 may be a circuit board. Circuit board 170 may have a groove 180 for receiving a proximal end 173 of member 174. This feature is further illustrated in FIG. 3, which is a perspective, top view of board 170.

In some embodiments, support member 174 may include an electrical contact 158 (e.g., a conductive pad or other device for conducting electricity) disposed on a surface thereof and electrically connected to source 118. The contact 158 electrically connects to a corresponding electrical contact 157 that may be disposed in groove 180 through an electrical interconnect 159 (e.g., a circuit trace or other transmission line). Contact 157 may be electrically connected to circuit 166 or other circuit on circuit board 170. Accordingly, in some embodiments, there is an electrical path from circuit 166 to source 118.

As further shown in FIG. 1, a reflector 176 may be attached to board 170 at an end thereof. Preferably, reflector 176 is attached to board 170 so that a face portion 177 of reflector 176 is generally perpendicular to side 171 and faces source 118. Preferably, face 177 reflects radiation emitted by source 118. For example, face 177 may have a reflective coating disposed thereon or face 177 may be constructed from a reflective material.

Figure 3:
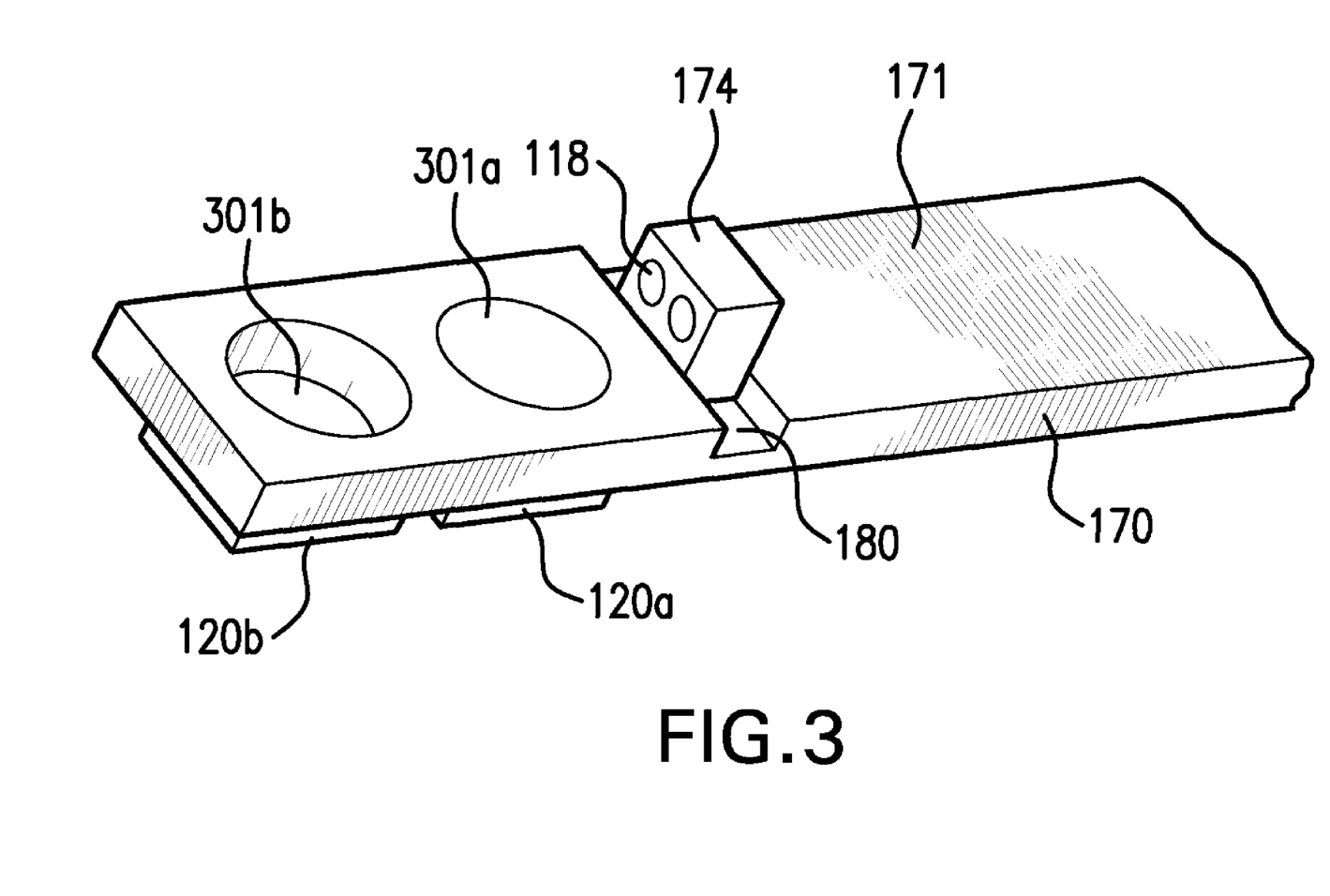
FIG. 3 is a perspective, top view of a circuit board according to an embodiment of the invention.

Referring now to photodetectors 120, photodetectors 120 are preferably disposed below a region of side 171 located between source 118 and reflector 176. For example, in some embodiments, photodetectors 120 are mounted to a bottom side 175 of board 170 at a location that is below a region between source 118 and reflector 176. In embodiments where the photodetectors 120 are mounted to bottom side 175 of board 170, a hole for each photodetector 120 is preferably created through board 170. This is illustrated in FIG. 3. As shown in FIG. 3, two holes 301a and 301b have been created in board 170, thereby providing a passageway for light from indicator molecules 116 to reach photodetectors 120. The holes in circuit board 170 may be created by, for example, drilling, laser machining and the like. Preferably, each photodetector 120 is positioned such that light entering the hole is likely to strike a photosensitive side of the photodetector 120, as shown in FIG. 1. This technique also diminishes the amount of ambient light striking photodetector 120.

As further illustrated in FIG. 1, each hole in board 170 may be contain a filter 134 so that light can only reach a photodetector 120 by passing through the corresponding filter 134. The bottom side and all sides of the photodetectors 120 may be covered with black light blocking epoxy 190 to further diminish the amount of ambient light striking photodetector 120.

In one embodiment, photodetector 120a is used to produce a signal corresponding to the light emitted or adsorbed by indicator molecules 116 and photodetector 120b is used to produce a reference signal. In this embodiment, a fluorescent element 154 may be positioned on top of filter 134b. Preferably, fluorescent element 154 fluoresces at a predetermined wavelength. Element 154 may be made from terbium or other fluorescent element that fluoresces at the predetermined wavelength. In this embodiment, filter 134a and filter 134b filter different wavelengths of light. For example, filter 134a may filter wavelengths below 400 nm and filter 134b may filter wavelengths below 500 nm.

Figure 2:
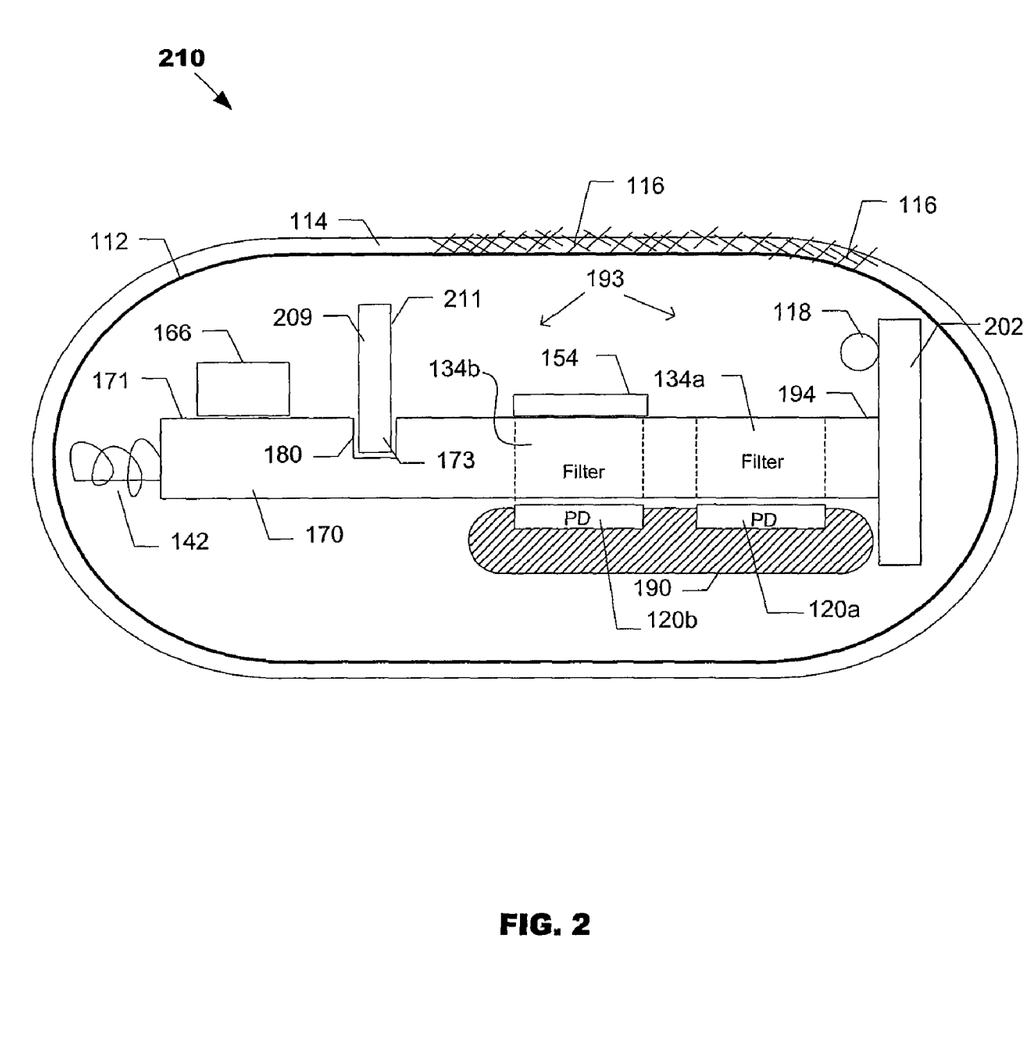
FIG. 2 is a schematic, section view of a fluorescence-based sensor according to another embodiment of the invention.

Referring now to FIG. 2, FIG. 2 illustrates a sensor 210 according to another embodiment of the invention. As shown in FIG. 2, sensor 210 is similar to sensor 110. A primary difference being that reflector 176 is replaced by a support member 202, which is connected to end 194 of board 170 and to which source 118 is fixed. In this embodiment, and support member 174 is replaced with a reflector 209. Like reflector 176, reflector 209 has a reflective face 211 that faces source 118. Additionally, so that photodetector 120a remains closer to source 118, photodetector 120a may switch places with photodetector 120b and filter 134a may switch places with filter 134b. Fluorescent element 154 may also be re-positioned so that it remains on top of filter 134b.

As shown in FIGS. 1 and 2, in some embodiments, indicator molecules 116 may be positioned only in a region that is above a region 193, which region is between source 118 and reflector 176.

Figure 4:
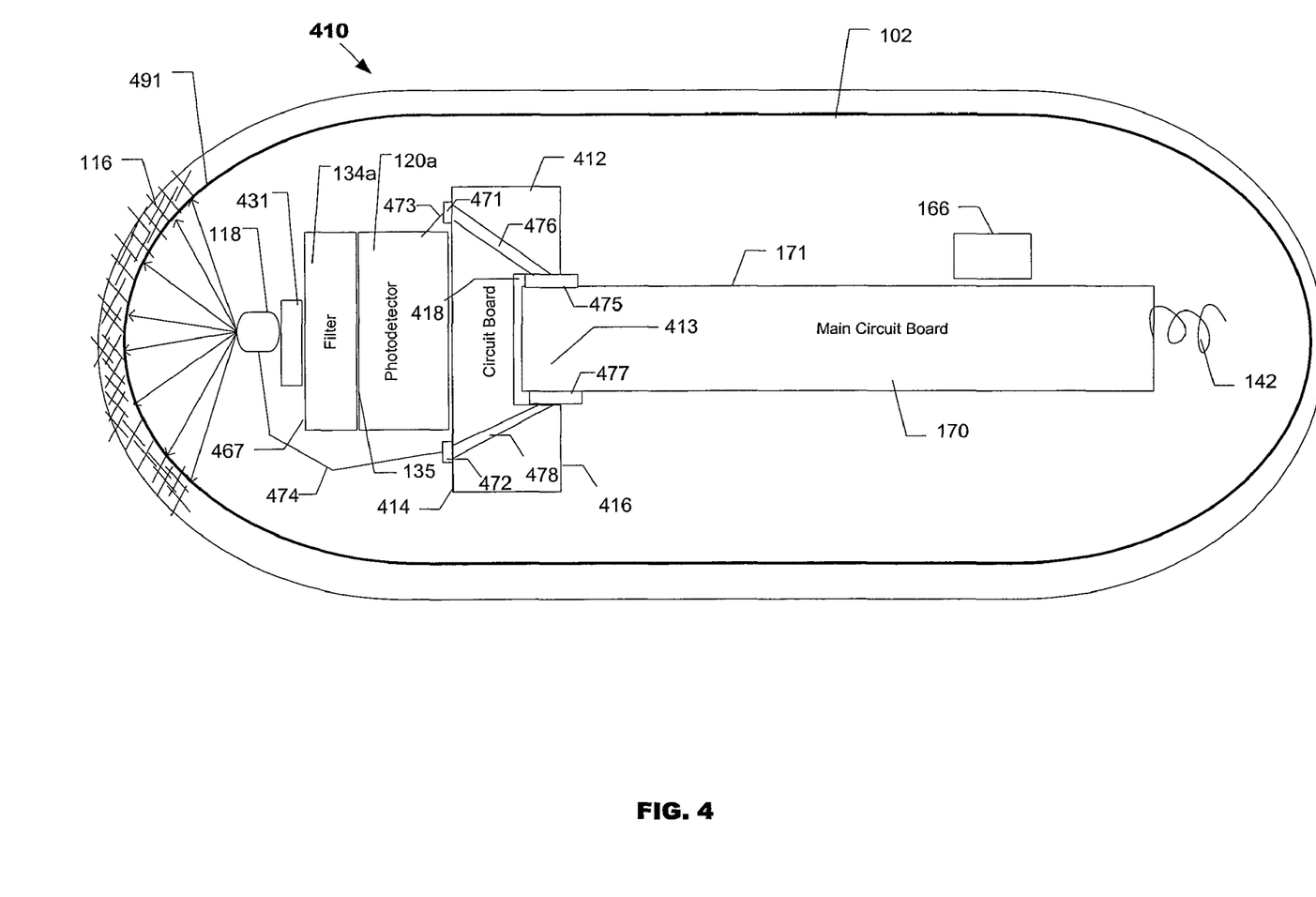
FIG. 4 is a schematic, section view of a fluorescence-based sensor according to another embodiment of the invention.

Referring now to FIG. 4, FIG. 4 is a schematic, section view of an optical-based sensor 410, according to another embodiment of the invention. Sensor 410 includes many of the same components as sensor 110. However, the positioning of source 118, photodetector 120a and filter 134a in sensor 410 is different than the positioning in sensor 110.

As shown in FIG. 4, a base 412 is mounted to an end 413 of circuit board 170. A top side 414 and bottom side 416 of base 412 each may lie in a plane that is generally perpendicular to a plane in which side 171 of board 170 lies. Bottom side 416 may have a groove 418 therein that receives end 413 of board 170. Groove 418 facilitates fixing base 412 to board 170.

Photodetector 120a may be mounted on top side 414 of base 412. Preferably, photodetector 120a is mounted on base 412 so that photosensitive side 135 of photodetector 120a lies in a plane that is generally perpendicular to the plane in which side 171 of board 170 lies and faces in the same direction as top side 414.

Filter 134a is preferably disposed above side 135 of photodetector 120a so that most, if not all, light that strikes side 135 must first pass through filter 134a. Filter 134a may be fixedly mounted to photodetector 120a. For example, a reflective index (RI) matching epoxy 501 (see FIG. 5) may be used to fix filter 134a to photodetector 120a.

In some embodiments, base 412 may include at least two electrical contacts disposed thereon (e.g., on side 414). For example, as shown in FIG. 4, a first electrical contact 471 and a second electrical contact 472 are disposed on side 414 of base 412. A wire 473 (or other electrical connector) preferably electrically connects photodetector 120a to electrical contact 471 and a wire 474 (or other electrical connector) preferably electrically connects source 118 to electrical contact 472. Contact 471 electrically connects to a corresponding contact 475 via an electrical interconnect 476. Similarly, contact 472 electrically connects to a corresponding contact 477 via an electrical interconnect 478. Contacts 475, 477 are preferably disposed on the end of board 170 that is inserted into groove 418. Contacts 475, 477 may be electrically connected to circuit 166 or other circuit on circuit board 170. Accordingly, in some embodiments, base 412 provides a portion of an electrical path from circuit 166 to source 118 and/or photodetector 120a.

Figure 5:
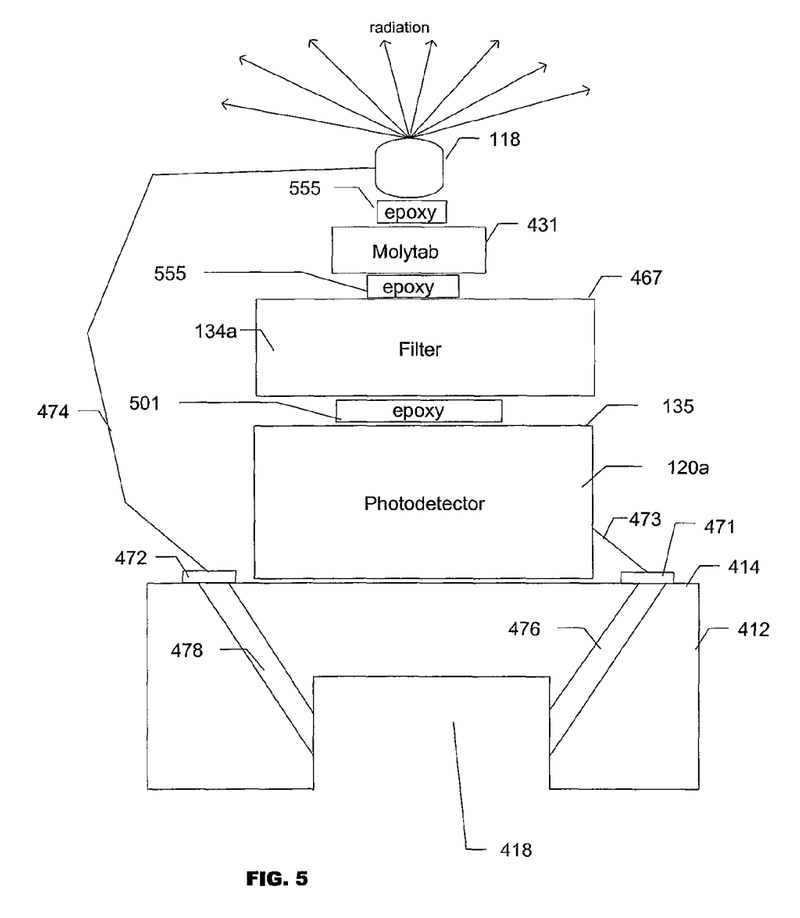
FIG. 5 is a schematic, section view of an assembly according to an embodiment of the invention.

Referring now to FIG. 5, FIG. 5 further illustrates the arrangement of photodetector 120a, filter 134a and source 118. As shown in FIGS. 4 and 5, source 118 is mounted on a top side 467 of filter 134a. Accordingly, as shown in FIGS. 4 and 5, photodetector 120a, filter 134a and source 118 are aligned. That is, as shown in FIG. 5, both filter 134a and source 118 are each disposed in an area that is over at least a portion of photosensitive side 135 of photodetector 120a.

Preferably, a non-transparent, non-translucent base 431 is disposed between source 118 and filter 134. Opaque base 431 functions to prevent light emitted from source 118 from striking side 467 of filter 134a. Base 431 may be a gold-clad-molybdenum tab (molytab) or other opaque structure. Epoxy 555 may be used to fix source 118 to base 431 and base 431 to filter 134a.

Preferably, in this embodiment, source 118 is configured and oriented so that most of the light transmitted therefrom is transmitted in a direction away from side 467, as shown in FIGS. 4 and 5. For example, in the embodiment shown, the light is primarily directed towards an end 491 of housing 102. Preferably, indicator molecules 116 are located on end 491 so that they will receive the radiation emitted from source 118. As discussed above, indicator molecules 116 will respond to the received radiation, and the response will be a function of the concentration of the analyte being measured in the region of the indicator molecules 116. Photodetector 120a detects the response.

Figure 6:
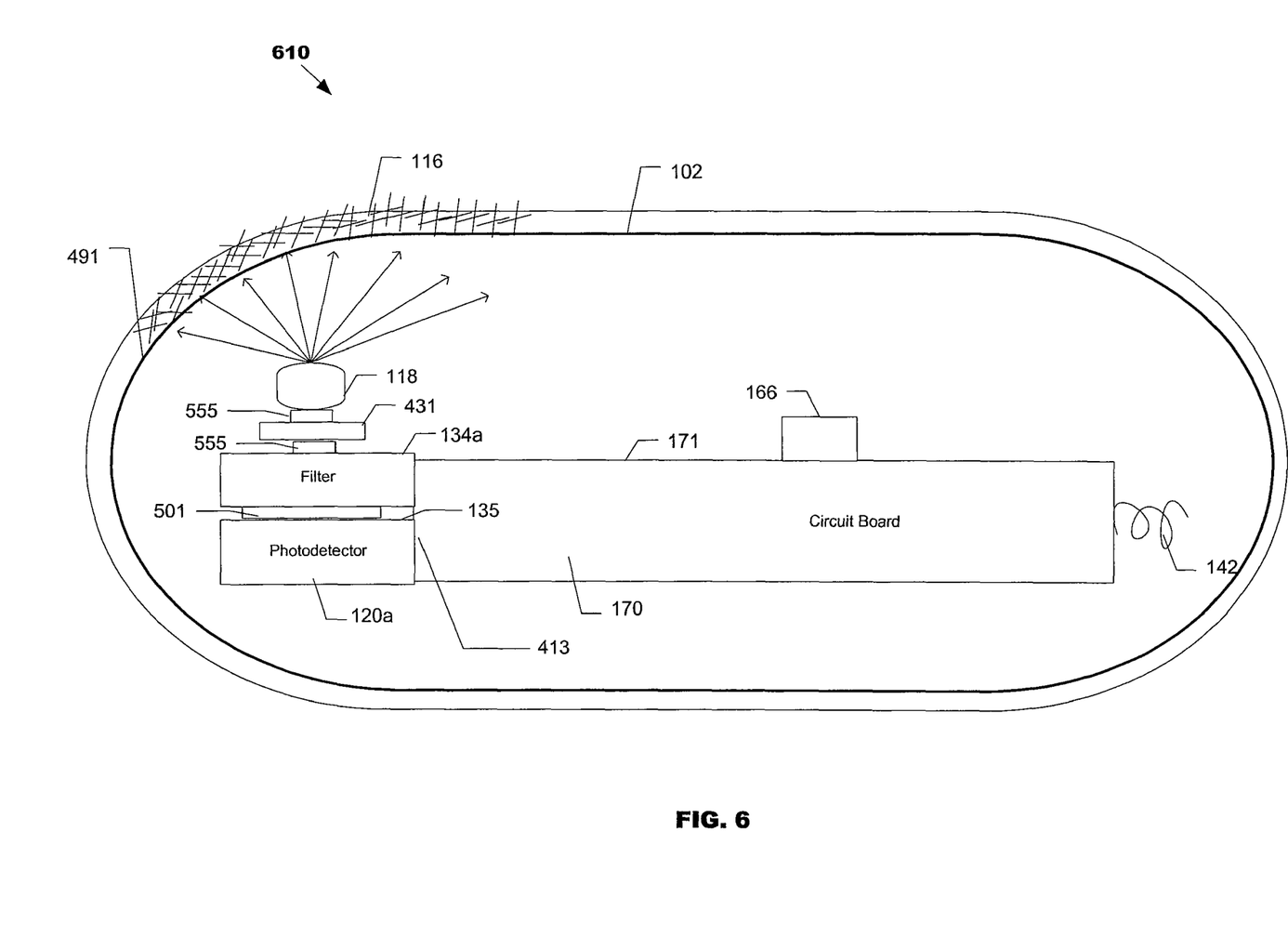
FIG. 6 is a schematic, section view of a fluorescence-based sensor according to another embodiment of the invention.

Referring now to FIG. 6, FIG. 6 is a schematic, section view of an optical-based sensor 610, according to another embodiment of the invention. Sensor 610 includes many of the same components as sensor 110. Also, sensor 610 is similar to sensor 410 in that, in sensor 610, photodetector 120a, filter 134a and source 118 are preferably aligned. Further, like in sensor 410, in sensor 610 filter 134a may be fixedly mounted on side 135 of photodetector 120a and source 118 may be fixedly mounted on side 467 of filter 134a, and the photodetector 120a, filter 134a, source 118 assembly may be located adjacent an end 491 of housing 102, as illustrated in FIG. 6.

However, the orientation of source 118, photodetector 120a and filter 134a in sensor 610 is different than the orientation in sensor 410. For example, in sensor 610, side 135 of photodetector 120a faces in a direction that is substantially perpendicular to the longitudinal axis of housing 102. Additionally, in sensor 610, filter 134a and/or photodetector 120a are directly fixed to board 170 such that base 412 may be removed. In the embodiment shown, filter 134a and/or photodetector 120a are directly fixed to end 413 of board 170.

In one or more of the above described embodiments, housing 102 may be filled with a material to keep the components housed in housing 102 from being able to move around. For example, housing 102 may be filled with an optical epoxy either before or after board 170 and the components attached thereto are inserted into housing 120. EPO-TEK 301-2 Epoxy from Epoxy Technology of Billerica, Mass. and/or other epoxies may be used.

While various embodiments/variations of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

What is claimed is:

1. An electro-optical sensing device for detecting the presence or concentration of an analyte, comprising:
    a housing having an outer surface;
    a plurality of indicator molecules located on at least a portion of the outer surface of the housing;
    a circuit board housed within the housing;
    a first photodetector connected to the circuit board for detecting a response of the indicator molecules;
    a second photodetector connected to the circuit board for detecting the response of a reference fluorescent element;
    a radiation source positioned a distance above the photosensitive sides of the first and second photodetectors; and
    a reflector spaced apart from said radiation source and attached to said circuit board.

2. The sensing device of claim 1, further comprising first and second optical filters covering the photosensitive sides of the first and second photodetectors, respectively.

3. The sensing device of claim 2, wherein the circuit board has first and second holes, extending therethrough, in which the first and second optical filters are respectively disposed, and under which the first and second photodetectors are respectively attached to the bottom side of the circuit board.

4. The sensing device of claim 3, wherein the non-photosensitive sides of the first and second photodetectors are covered with black light-blocking epoxy.

5. The sensing device of claim 4, wherein the reference fluorescent element is terbium.

6. The sensing device of claim 3, wherein the reference fluorescent element is positioned on top of the second optical filter and fluoresces at a predetermined wavelength.

7. The sensing device of claim 2, wherein the first and second optical filters filter different wavelengths of light.

8. The sensing device of claim 1, further comprising a support member having a side that lies on a plane that is substantially perpendicular to a plane on which a top side of the circuit board lies;
    wherein the radiation source is attached to said side of the support member.

9. The sensing device of claim 8, wherein the circuit board has a groove in the top side thereof and the support member has an end inserted into the groove.

10. The sensing device of claim 8, wherein a first electrical contact is disposed on a surface of the support member and the radiation source is electrically connected to the electrical contact.

11. The sensing device of claim 10, wherein the first electrical contact is electrically connected to a second electrical contact disposed on the circuit board.

12. The sensing device of claim 11, further comprising a circuit trace disposed on or within the support member that functions to electrically connect the first electrical contact with the second electrical contact.

13. The sensing device of claim 1, wherein the distance ranges between about 0.010 inches and 0.030 inches.

14. The sensing device of claim 1, wherein said reflector has a reflective side that faces the radiation source.

15. The sensing device of claim 14, wherein the first and second photodetectors are positioned in a location beneath a region between the radiation source and the reflective side of the reflector.

16. The sensing device of claim 15, wherein the photosensitive sides of the first and second photodetectors face in a direction substantially perpendicular to the direction that the reflective side of the reflector faces.

17. The sensing device of claim 16, wherein the photosensitive sides of the first and second photodetectors are positioned below the top side of the circuit board.

18. An electro-optical sensing device for detecting the presence or concentration of an analyte, comprising:

a housing having an outer surface;

a plurality of indicator molecules located on at least a portion of the outer surface of the housing;

a circuit board housed within the housing;

a first photodetector connected to the circuit board for detecting a response of the indicator molecules;

a second photodetector connected to the circuit board for detecting the response of a reference fluorescent element;

a radiation source positioned a distance above the photosensitive sides of the first and second photodetectors; and a reflector spaced apart from the radiation source and having a reflective side that faces the radiation source;

wherein said circuit board has a groove in the top side thereof and said reflector has an end inserted into said groove.

* * * * *